(12) United States Patent
Matsuo

(10) Patent No.: US 8,206,287 B2
(45) Date of Patent: Jun. 26, 2012

(54) ENDOSCOPE HAVING FLEXIBLE TUBE

(75) Inventor: Shigeki Matsuo, Tokyo (JP)

(73) Assignee: Olympus Corporation, Tokyo (JP)

( * ) Notice: Subject to any disclaimer, the term of this patent is extended or adjusted under 35 U.S.C. 154(b) by 576 days.

(21) Appl. No.: 11/884,297

(22) PCT Filed: Feb. 10, 2006

(86) PCT No.: PCT/JP2006/302382
§ 371 (c)(1),
(2), (4) Date: Aug. 14, 2007

(87) PCT Pub. No.: WO2006/085621
PCT Pub. Date: Aug. 17, 2006

(65) Prior Publication Data
US 2008/0214897 A1    Sep. 4, 2008

(30) Foreign Application Priority Data

Feb. 14, 2005 (JP) ................................. 2005-036970

(51) Int. Cl.
*A61B 1/00* (2006.01)
(52) U.S. Cl. ........................................ 600/140; 600/141
(58) Field of Classification Search ................. 600/139, 600/144, 130, 146, 141, 142, 140, 143, 145, 600/149
See application file for complete search history.

(56) References Cited

U.S. PATENT DOCUMENTS

| 4,530,568 A | * | 7/1985 | Haduch et al. | ................. | 385/118 |
| 5,179,935 A | * | 1/1993 | Miyagi | ........................... | 600/142 |
| 5,386,816 A | * | 2/1995 | Inoue et al. | ................... | 600/121 |

(Continued)

FOREIGN PATENT DOCUMENTS

| EP | 0 535 847 A | 4/1993 |
| JP | 01-129828 | 5/1989 |

(Continued)

OTHER PUBLICATIONS

Extended Supplementary European Search Report dated Nov. 25, 2009.

*Primary Examiner* — Anhtuan Nguyen
*Assistant Examiner* — Alireza Nia
(74) *Attorney, Agent, or Firm* — Scully, Scott, Murphy & Presser, P.C.

(57) ABSTRACT

A flexible tube for an endoscope and an endoscope device are provided. According to the present invention, a flexible tube for an endoscope is included in an insertion portion of the endoscope to be inserted into a body cavity and the flexible tube for the endoscope includes a bending portion provided at a distal end side and configured to perform a bending operation corresponding to an operation of an operator, and a flexible tube portion having a distal end and a proximal end and the distal end is connected to a proximal end side of the bending portion. The bending portion has a region that is bent at a first curvature radius when the bending portion is maximally bent, and at the distal end side of the flexible tube portion, a region that is set to be bent at a second curvature radius smaller than the first curvature radius when the bending portion is passively bent by a predetermined force quantity is provided. Accordingly, resistance which occurs when the bending portion is passing through the intestine bending portion is suppressed and an insertion performance of the insertion portion is increased. Thus, patients are less burdened and less painful.

2 Claims, 10 Drawing Sheets

U.S. PATENT DOCUMENTS

| | | | |
|---|---|---|---|
| 5,681,263 A * | 10/1997 | Flesch | 600/141 |
| 5,897,537 A * | 4/1999 | Berg et al. | 604/525 |
| 5,911,715 A * | 6/1999 | Berg et al. | 604/525 |
| 5,916,147 A * | 6/1999 | Boury | 600/146 |
| 6,402,687 B1 * | 6/2002 | Ouchi | 600/139 |
| 6,482,149 B1 * | 11/2002 | Torii | 600/142 |
| 6,485,411 B1 * | 11/2002 | Konstorum et al. | 600/139 |
| 6,585,641 B1 * | 7/2003 | Jordfald | 600/144 |
| 6,648,874 B2 * | 11/2003 | Parisi et al. | 604/525 |
| 6,811,532 B2 * | 11/2004 | Ogura et al. | 600/146 |
| 7,326,176 B2 * | 2/2008 | Machiya et al. | 600/142 |
| 7,678,117 B2 * | 3/2010 | Hinman et al. | 606/108 |
| 2002/0028984 A1 | 3/2002 | Hayakawa et al. | |
| 2004/0044270 A1 * | 3/2004 | Barry | 600/142 |
| 2006/0041188 A1 * | 2/2006 | Dirusso et al. | 600/146 |

FOREIGN PATENT DOCUMENTS

| | | |
|---|---|---|
| JP | 05-031065 | 2/1993 |
| JP | 2002-000552 | 1/2002 |
| JP | 2002-065592 | 3/2002 |

* cited by examiner

ENDOSCOPE HAVING FLEXIBLE TUBE

TECHNICAL FIELD

The present invention relates to flexible tube which has a flexible insertion portion used for an endoscope and an endoscope device.

BACKGROUND ART

Conventionally, in the medical field, endoscopes are used, for example, by inserting an elongated insertion portion into a body cavity to observe an organ in the body cavity, for example, a large intestine, or to perform various treatments using a treatment instrument which is inserted into a treatment instrument insertion channel if necessary.

When the insertion portion of the endoscope is inserted into the body cavity, a user, who is an operator, grasps a flexible tube portion (flexible portion) and, while pushing the portion into the body cavity, bends an bending portion (angle portion) in a desired direction by performing a predetermined operation of an operation knob which is provided in an operation portion of the endoscope.

For example, in Japanese Unexamined Patent Application Publication No. 5-31065, an insertion portion of an endoscope is proposed. In the endoscope insertion portion, in order from a distal end, a distal end rigid portion, an angle portion, and a flexible portion are provided. In the endoscope, spiral pipes provided the inside and outside of the insertion portion are spot-welded at predetermined pitch intervals in the axis line direction. In the endoscope, the spot-welded portions become joints and become hard due to increased resistance against the bending. Further, the endoscope has a characteristic structure that as the welding pitch intervals become narrow, the hardness increases.

Further, in the endoscope, at a root side of the insertion portion, that is, at a connection side to a main body operation portion, the welding pitch intervals become short, and at a distal end side, that is, at a connection side to the angle portion, the welding pitch intervals are varied to be wide in order to substantially continuously vary the hardness from the root side to the distal end side of the insertion portion.

When the insertion portion of the endoscope described in the above-described Japanese Unexamined Patent Application Publication No. 5-31065 passes through a bending portion in the body cavity, the flexible portion is bent while following along the body cavity wall.

However, the angle portion of the endoscope becomes a bending state greater than the bending state of the flexible portion having a predetermined hardness depending on the bending degree of the operation. That is, independently of the bending state of the body cavity or the bending state, the bending portion locally becomes a large bending state against the flexible portion in response to the bending operation of the operator.

The bending portion being in the bending state, according to the force quantity pressed by the user, presses the bending body cavity wall, and further, rapidly bends the body cavity. Then, the bending portion is hooked at the rapidly bent body cavity wall. Accordingly, the body cavity is heavily burdened and is drawn more than necessary. As a result, the patient is largely burdened at the endoscopy, and is distressed.

Accordingly, the present invention has been made in view of the above, and an object is to provide an endoscope which suppresses resistance occurs when the bending portion passes through the bending portion of the body cavity at the endoscopic inspection and increase insertion performance of the insertion portion to reduce the burden and pain to patients.

DISCLOSURE OF INVENTION

Means for Solving the Problem

To achieve the above object, in a first flexible tube of an endoscope and a first endoscope device of the present invention, a flexible tube for an endoscope included in an insertion portion of the endoscope to be inserted into a body cavity includes a bending portion provided at a distal end side and configured to perform a bending operation corresponding to an operation of an operator, and a flexible tube portion having a distal end and a proximal end and the distal end is connected to a proximal end side of the bending portion. The bending portion has a region that is bent at a first curvature radius when the bending portion is maximally bent, and at the distal end side of the flexible tube portion, a region that is set to be bent at a second curvature radius smaller than the first curvature radius when the bending portion is passively bent by a predetermined force quantity is provided.

Further, in a second flexible tube of an endoscope and a second endoscope device of the present invention, a flexible tube for an endoscope included in an insertion portion of the endoscope to be inserted into a body cavity includes a bending portion provided at a distal end side and configured to perform a bending operation corresponding to an operation of an operator, and a flexible tube portion having a distal end and a proximal end and the distal end is connected to a proximal end side of the bending portion. The bending portion has a region that is bent at a first curvature radius when the bending portion is maximally bent, and the flexible tube portion includes a region that is maximally bent at a second curvature radius smaller than the first curvature radius at the distal end side, and the portion includes, at the proximal end side than the region that is bent at the second curvature radius, a region that is bent at a third curvature radius larger than the first and second curvature radiuses.

Further, in a third flexible tube of an endoscope and a third endoscope device of the present invention, a flexible tube for an endoscope included in an insertion portion of the endoscope to be inserted into a body cavity includes a bending portion provided at a distal end side and configured to perform a bending operation corresponding to an operation of an operator, and a flexible tube portion whose distal end is connected to a proximal end side of the bending portion, and has a distal end region and a proximal end region. The bending portion has a region that is bent at a first curvature radius when the bending portion is maximally bent, and at the distal end region, a first region that is set to be bent at a second curvature radius smaller than the first curvature radius when the bending portion is passively bent by a predetermined force quantity is provided, and, at the proximal end side than the first region, a second region that is set to be bent at a third curvature radius larger than the first curvature radius and the second curvature radius by the predetermined force quantity is provided.

BEST MODE FOR CARRYING OUT THE INVENTION

First Embodiment

Hereinafter, the first embodiment of the present invention will be described with reference to the drawings.

Figure 1:
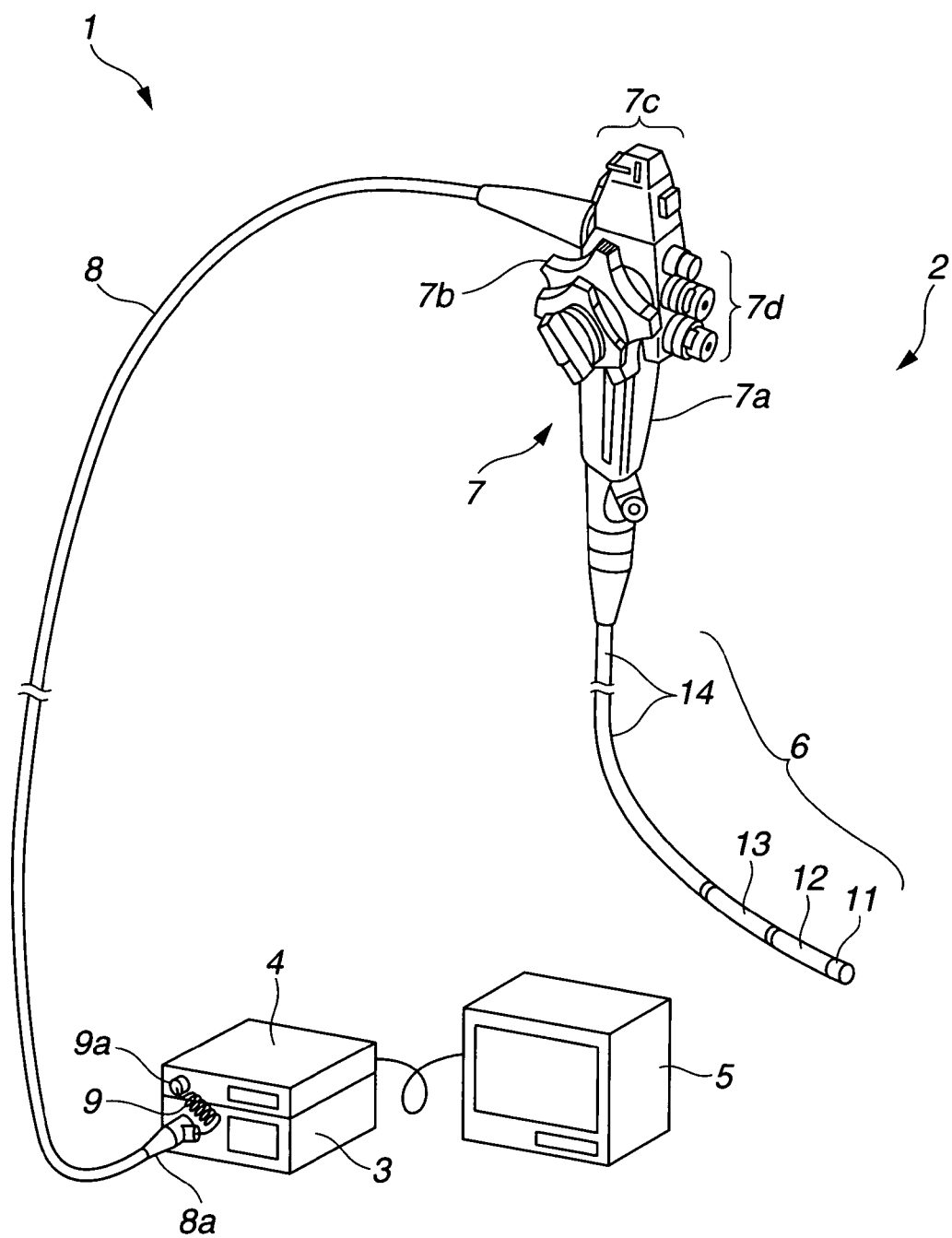
FIG. 1 is a view illustrating a schematic configuration of an endoscope device having an endoscope according to a first embodiment.

FIG. 1 is a view illustrating a schematic configuration of an endoscope device having an endoscope.

As shown in FIG. 1, an endoscope device 1 includes an electronic endoscope (hereinafter, abbreviated to endoscope) 2 which has image pickup means (not shown), a light source device 3 which provides illumination light, a processor 4 which generates a video signal by an electric signal transmitted from the image pickup means of the endoscope 2, and a monitor 5 functions as a display device which receives the video signal and displays an endoscopic image.

The endoscope 2 according to the present embodiment includes an insertion portion 6 which is a long flexible tube for the endoscope to be inserted into a body cavity, an operation portion 7 which is positioned at a proximal end side of the insertion portion 6, and a universal code 8 which extends from one side portion of the operation portion 7 as main components.

The operation portion 7 includes a grasping portion 7a, a bending operation knob 7b, various switches 7c which instruct a release of the image pickup means or the like, and various buttons 7d such as an air/water feed button.

To a distal end portion of the extended side of the universal code 8, an endoscope connector 8a which is detachably connected to the light source device 3 which is an external device is provided. From the endoscope connector 8a, an electric cable 9 which has an electric connector 9a to be connected to the processor 4 which is an external device is extended.

The insertion portion 6 of the endoscope 2 includes, in order from the distal end side, a distal end configuration portion 11, a bending portion 12, a curvature transition portion 13 which is a first flexible tube portion, and a force quantity transmission portion 14 which is a second flexible tube portion. That is, the curvature transition portion 13 and the force quantity transmission portion 14 constitute a flexible tube portion in the insertion portion 6.

To the curvature transition portion 13, when the insertion portion 6 is inserted into the body cavity, a predetermined quantity of pressure force applied to the force quantity transmission portion 14 is transmitted. In response to the force quantity, the curvature transition portion 13 inserted into the body cavity is passively bent when the curvature transition portion 13 comes in contact with a bending body cavity wall.

Further, the curvature transition portion 13 includes a portion at a distal end side (distal end region), the portion in which a curvature radius at a maximum bending state is set to be smaller than a curvature radius of the bending portion 12 at a maximum bending state formed when the bending portion 12 is operated to bend or the bending portion 12 is passively bent. Further, the curvature transition portion 13 is set such that the curvature radius is gradually increased from the distal end side toward a proximal end side (proximal end region). The distal end side of the curvature transition portion 13 is a side connected to the bending portion 12, and the proximal end side of the curvature transition portion 13 is a side connected to the force quantity transmission portion 14.

The force quantity transmission portion 14 is, in response to a predetermined quantity of pressure force, also passively bent when the force quantity transmission portion 14 comes in contact with the bending body cavity wall.

Further, the curvature transition portion 13 is set such that a curvature radius in a maximum bending state becomes smaller than a curvature radius in a maximum bending state formed when the force quantity transmission portion 14 is passively bent by the predetermined quantity of pressure force.

That is, the insertion portion 6 is set such that when the insertion portion 6 is maximally bent, bending radius/curvature is varied at substantially constant rates. In other words, to the insertion portion 6, in order from the distal end, the bending portion 12, the curvature transition portion 13, and the force quantity transmission portion 14 are provided such that the bending radius/curvature is varied at the substantially constant rates. With respect to the above-described bending state in the insertion portion 6, detailed description will be made below.

In the distal end configuration portion 11, an image pickup unit (not shown) which includes an image pickup device such as a CCD or a CMOS which functions as image pickup means, a circuit board which drives the image pickup device, an observation optical system, and the like is provided. Further, to the distal end configuration portion 11, a distal end portion of a light guide in which illumination light for illuminating an observation target portion in the body cavity passes through is provided. In the distal end configuration portion 11, an illumination unit which includes a light guide, an illumination optical system, and the like is provided.

Figure 2:
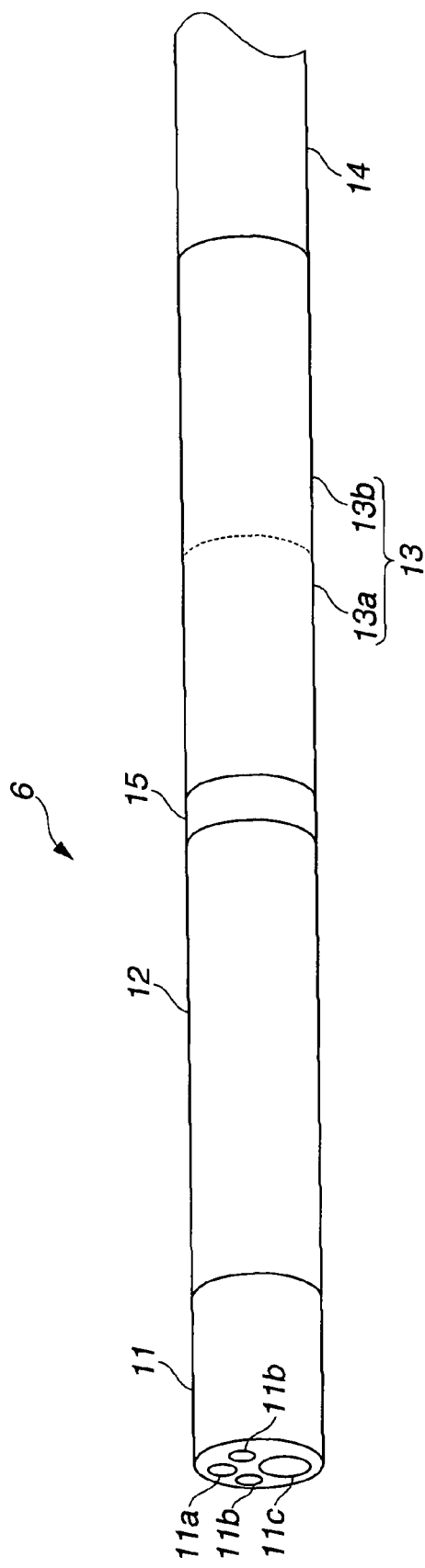
FIG. 2 is a view for explaining a distal end portion of an insertion portion according to the first embodiment.
Figure 3:
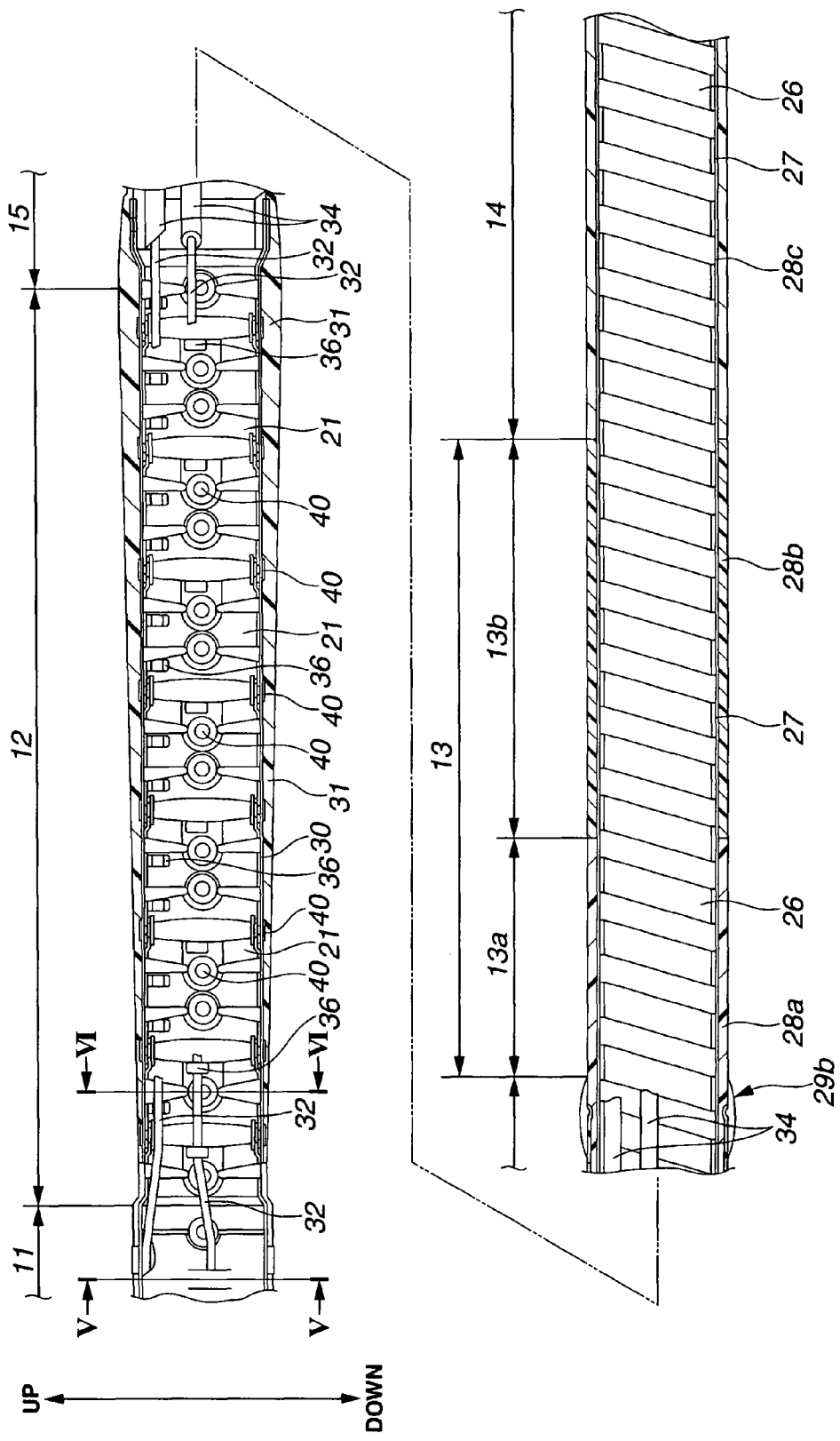
FIG. 3 is a cross sectional view of the distal end portion of the insertion portion cut along a longitudinal direction according to the first embodiment.
Figure 4:
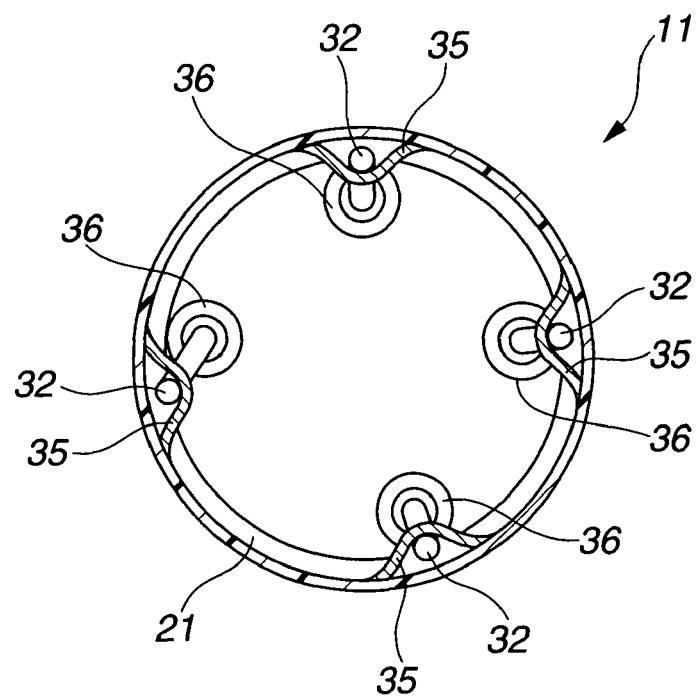
FIG. 4 is a cross sectional view of the distal end portion taken along the IV-IV line of FIG. 3 according to the first embodiment.
Figure 5:
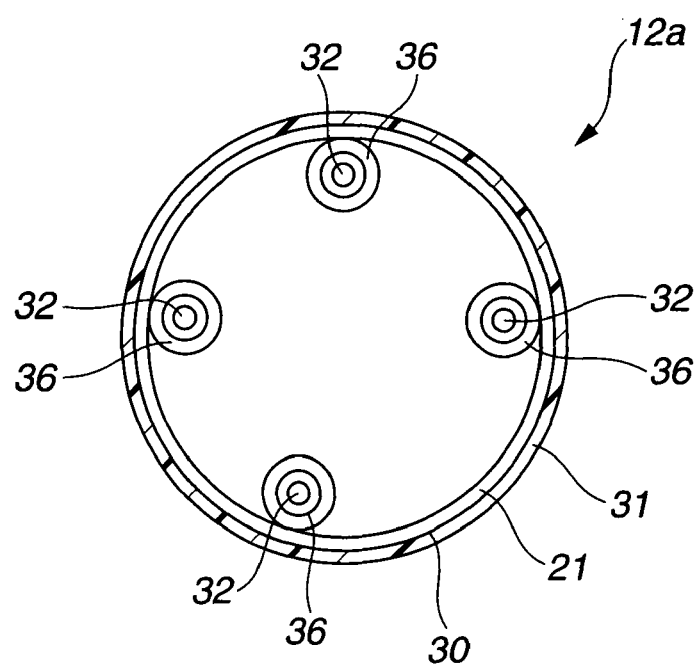
FIG. 5 is a cross sectional view of a first bending portion taken along the V-V line of FIG. 3 according to the first embodiment.

Now, with reference to FIGS. 2 to 5, configurations of the distal end configuration portion of the insertion portion, the bending portion, the curvature transition portion, and the flexible tube portion will be described. FIG. 2 is a view for explaining the distal end portion of the insertion portion, FIG. 3 is a cross sectional view of the distal end portion of the insertion portion cut along a longitudinal direction, FIG. 4 is a cross sectional view of the distal end portion taken along the IV-IV line of FIG. 3, and FIG. 5 is a cross sectional view of the first bending portion taken along the V-V line of FIG. 3.

As shown in FIG. 2, the distal end configuration portion 11 provided at the distal end of the insertion portion 6 includes, on a distal end surface, an observation window 11a which has an observation lens and the like, for example, two illumination windows 11b which have illumination lenses and the like, and an opening portion 11c of a forceps channel through which a forceps or the like which is a treatment instrument is inserted.

The bending portion 12 which is connected to the proximal end side of the distal end configuration portion 11 has a length of, for example, about 70 mm to 80 mm in an insertion axis direction.

The curvature transition portion 13 which is connected to the bending portion 12 includes, in order from the distal end side, two portions, that is, a first curvature transition portion 13a and a second curvature transition portion 13b. The first curvature transition portion 13a has a length of, for example, about 20 mm to 25 mm in the insertion axis direction, and the second curvature transition portion 13b has a length of, for example, about 30 mm to 40 mm in the insertion axis direction.

As shown in FIG. 3, the bending portion 12 includes a plurality of bending pieces 21 (also referred to as bending nodal rings) which are rotatably connected with joint portions 40 respectively. The bending piece 21 of a most distal end is provided at the proximal end side of the distal end configuration portion 11.

On the plurality of the bending pieces 21, a bending braid 30 formed by weaving thin wires or the like in a cylindrical shape is covered, and further, on the bending braid 30, an outer cover 31 which is a first exterior tube body having a predetermined flexibility to maintain water tightness is covered. Thus, the bending portion 12 is formed at the distal end side of the insertion portion 6.

The outer cover 31 is formed such that a thickness of a portion covering the bending portion 12 is gradually increased from a distal end side. Accordingly, the bending portion 12 is set such that the flexural rigidity is gradually increased from the distal end to the proximal end by the flexibility of the outer cover 31.

Further, into the insertion portion 6, four bending operation wires (also referred to as angle wires) 32 are inserted to perform a bending operation of the bending portion 12 by pulling or loosening the bending portion 12 from the distal end side. These bending operation wires 32 are inserted into wire guides 36 in the bending portion 12 and held. Proximal end sides of the bending operation wires 32 are respectively inserted into coil sheathes 34 from the connection portion 15. The coil sheathes 34 employed in the present embodiment are formed by closely coiling wires like a pipe to have incompressible configurations.

The bending operation wires 32 are, as shown in FIG. 4, at the proximal end side of the distal end configuration portion 11, the respective distal end portions are held and fixed by fixing members 35 at four points spaced apart in substantially vertical and horizontal directions toward the surface of the sheet of FIG. 4.

Further, the proximal ends of the bending operation wires 32 are connected to a bending operation mechanism (not shown) which is provided in the operation portion 7 (see FIG. 1), and alternately pulled or loosened. The bending operation mechanism is connected to the bending operation knob 7b which is provided in the operation portion 7.

The bending operation wires 32 are pulled or loosened by a predetermined operation of the bending operation knob 7b. Accordingly, the bending portion 12 is operated to bend in the four directions by pulling or loosening the respective four bending operation wires 32.

As shown in FIGS. 3 and 5, the bending pieces 21 in the bending portion 12 are, the two wire guides 36 into which the bending operation wires 32 are inserted and held are fixed on an inner circumferential surface in the vicinity of the proximal end surface side by means of welding or the like.

The two wire guides 36 are provided at positions on the inner circumference surface shifted each other by substantially 180 degrees in a circumferential direction around an insertion axis dividing respective circumferences of the bending pieces 21, and at positions shifted each other by substantially 90 degrees in a circumferential direction around an insertion axis with respect to a pair of the joint portions 40. That is, the two wire guides 36 are provided at the positions on the inner circumference surface of respective bending pieces 21 where the line connecting the wire guides 36 with each other substantially divides the respective bending pieces 21 into substantially half in the insertion axis direction and substantially orthogonal to the line connecting the pair of the joint portions 40.

In the curvature transition portion 13 and in the force quantity transmission portion 14, a flex tube 26 which is a spiral tube is inserted. On an outer circumference of the flex tube 26, similarly to the bending portion 12 and the curvature transition portion 13, a braid 27 is covered.

On the first and second curvature transition portions 13a and 13b, and the force quantity transmission portion 14, outer covers which have different flexibilities respectively are covered on the braid 27.

On the first curvature transition portion 13a, an outer cover 28a whose flexibility at a distal end side (connection side to the bending portion 12) is higher than that of a proximal end portion of an outer cover 31 of the bending portion 12, and, the flexibility is set to be gradually decreased from the distal end side to a proximal end side (connection side to the second curvature transition portion 13b), and which is to be a second exterior tube body, is covered on the braid 27. Accordingly, the first curvature transition portion 13a is set such that the flexural rigidity is gradually increased from the distal end to the proximal end by the flexibility of the outer cover 28a.

On the second curvature transition portion 13b, an outer cover 28b whose flexibility is lower than that of the proximal end portion of the second outer cover 28a of the first curvature transition portion 13a, and, the flexibility is set to be gradually decreased from a distal end side (connection side to the first curvature transition portion 13a) to a proximal end side (connection side to the force quantity transmission portion 14), and which is to be a third exterior tube body, is covered on the braid 27. Accordingly, the second curvature transition portion 13b is set such that the flexural rigidity is gradually increased from the distal end to the proximal end by the flexibility of the outer cover 28b.

The respective outer covers 28a and 28b of the first and second curvature transition portions 13a and 13b of the curvature transition portion 13 are composed of a synthetic resin which has a predetermined rigidity mixed with a flexible resin, for example, polyurethane, and a hard resin, for example, polyester.

Further, in the respective outer covers 28a and 28b, a ratio of the flexible resin is higher in the distal end side, and the ration of the flexible resin is gradually decreased toward the proximal end, that is, being formed by the synthetic resin having high ratio of the hard resin. Accordingly, the rigidities of the respective outer covers 28a and 28b are gradually increased from the distal end side to the proximal end side. Then, the flexural rigidity of the whole curvature transition portion 13 is set to be gradually increased from the distal end side to the proximal end side.

On the force quantity transmission portion 14, an outer cover 28c whose flexibility is lower than that of the outer cover of the second curvature transition portion 13b, and, the flexibility is constant from a distal end side (connection side to the second curvature transition portion 13b) to a proximal end side (connection side to the operation portion 7), and which is to be a fourth exterior tube body, is covered on the braid. Accordingly, the force quantity transmission portion 14 is set such that the flexural rigidity is to be constant by the evenly set flexibility of the outer cover 28c. The outer cover 31 and the outer cover 28a are connected with each other in the connection portion 15 by a spool-adhesion portion 29b.

The outer cover 28c of the force quantity transmission portion 14 is composed of a synthetic resin which the flexible resin and the hard resin are evenly compounded in ratio over the whole length. Further, the outer cover 28c is formed to have a constant flexibility with a predetermined compound of the flexible resin and the hard resin such that the flexural rigidity of the force quantity transmission portion 14 is substantially similar to that of the proximal end side of the curvature transition portion 13.

Figure 6:
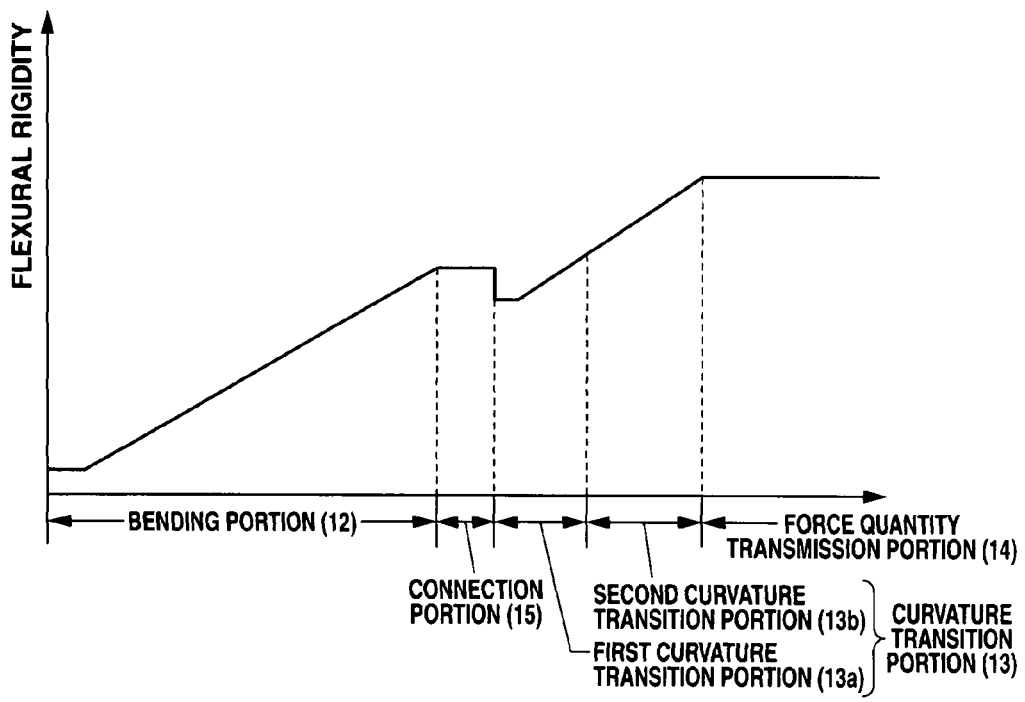
FIG. 6 is a graph illustrating variations of flexural rigidity of a bending portion, a curvature transition portion, and a flexible tube portion according to the first embodiment.

Accordingly, as shown in the graph of FIG. 6, the flexural rigidity of the bending portion 12 is set to be continuously increased at a constant rate from the distal end toward the proximal end to the connection portion 15.

Further, the flexural rigidity in the distal end portion of the first curvature transition portion 13a (first region) to the proximal end of the second curvature transition portion (second region) is also set to be continuously increased at a constant rate. A flexural rigidity of a most distal end of the first curvature transition portion 13a is set to be smaller than that of a most proximal end of the bending portion 12 by a predetermined value. The force quantity transmission portion 14 is formed to have a substantially similar flexural rigidity to that of the curvature transition portion 13 of a most proximal end over the whole length.

Figure 7:
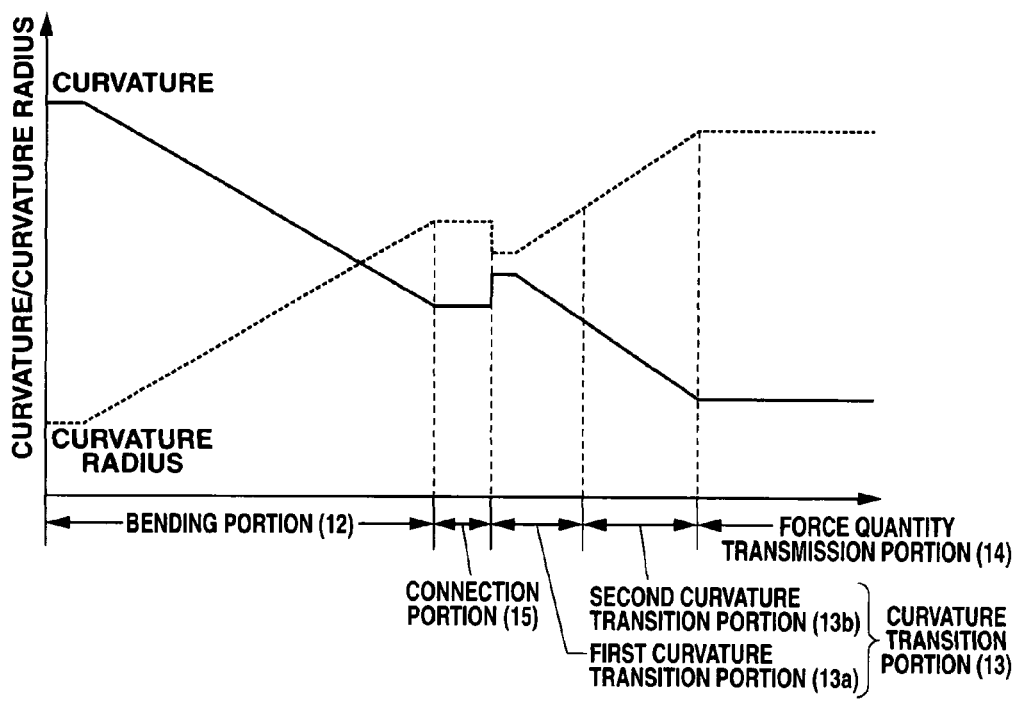
FIG. 7 is a graph illustrating variations of a curvature and a curvature radius at an insertion axis of a bending portion, a curvature transition portion, and a flexible tube portion according to the first embodiment.

Accordingly, for example, in the bending portion 12 which is bent when the bending portion 12 comes in contact with the bending body cavity wall with a predetermined quantity of pressure force (for example, a force quantity of about 2 kg at a maximum), as shown in the graph of FIG. 7, the curvature is highest at the insertion axis of the most distal end, and the curvature at the insertion axis is continuously decreased at a constant rate to the connection portion 15.

In the curvature transition portion 13 which is similarly bent, the curvature at the distal end portion of the first curvature transition portion 13a is higher than that of the connection portion 15 by a predetermined value, then, the curvature at the insertion axis is gradually decreased at a constant rate, and the curvature at the insertion axis of the most proximal end of the second curvature transition portion 13b is lowest.

In other words, in the insertion portion 6, the curvature radius at the insertion axis of the most distal end of the bending portion 12 which is operated to maximally bend by the operator has a smallest value. Then, in the insertion portion 6, a curvature radius (in the present embodiment, a second curvature radius) of the insertion axis from the connection portion 15 to the distal end portion of the first curvature transition portion 13a which is to be a second end portion (region) becomes smaller than a curvature radius (in the present embodiment, a first curvature radius) at the most proximal end of the bending portion 12 which is to be a first end portion (region) by a predetermined value. The curvature radius at the insertion axis continuously becomes larger values at a constant rate toward the proximal end.

Further, in the insertion portion 6, a curvature radius (in the present embodiment, a third curvature radius) at the insertion axis at the most proximal end of the second curvature transition portion 13b which is to be a third end portion (region) of the curvature transition portion 13 becomes a largest value, and the value of the largest curvature radius becomes to be constant over the whole length of the force quantity transmission portion 14.

That is, when the operator performs the bending operation of the bending portion 12 along an intestine bending portion such as a large intestine, and pushes the force quantity transmission portion 14 at a predetermined quantity of force (for example, a force quantity of about 2 kg at a maximum) in a direction of a deep portion of the large intestine, the bending portion 12 and the curvature transition portion 13 are bent along a bending portion of the body cavity by the contact with the bending body cavity wall. Then, the first curvature transition portion 13a can be bent to have a smaller curvature radius than that of the most proximal end of the bending portion 12. Accordingly, the first curvature transition portion 13a can readily follow the bending state of the bending portion 12, and is gently bent. Then, in the curvature transition portion 13, from the distal end side of the first curvature transition portion 13a to the proximal end side of the second curvature transition portion 13b, the curvature radius at the insertion axis in the bending state is increased at a constant rate.

As a result, the curvature transition portion 13 smoothly inserts the force quantity transmission portion 14 into the intestine bending portion in a gentle curve. That is, since the distal end side of the first curvature transition portion 13a is set to be readily bent as compared with the bending state at the proximal end side of the bending portion 12, the curvature transition portion 13 is readily bent starting at the distal end side of the first curvature transition portion 13a.

That is, the bending portion 12, the curvature transition portion 13, and the force quantity transmission portion 14 passing through the intestine bending portion are inserted into a deep part of the large intestine without being stuck at the bending intestinal wall. Further, since the flexural rigidity of the force quantity transmission portion 14 is higher than those of the bending portion 12 and the curvature transition portion 13, without being bent, the force quantity transmission portion 14 can surely transmit the pressure force quantity to the side of the curvature transition portion 13.

The bending portion 12 is set to have a large curvature radius at a constant rate from the distal end to the proximal end. Accordingly, if the operator performs the bending operation of the bending portion 12 along an intestine bending portion such as a large intestine, the bending portion 12 is bent to have a gently varying curvature from the distal end to the proximal end.

As a result, in the insertion portion 6 of the endoscope 2 according to the present embodiment, the curvature transition portion 13 readily follows the bending state of the bending portion 12, and the force quantity transmission portion 14 is smoothly introduced. Accordingly, the bending portion 12 and the curvature transition portion 13 smoothly pass though the intestine bending portion without rapid changing state of the intestine bending portion. Further, the resistance which occurs when the bending portion 12 is passing through the intestine bending portion can be suppressed. Accordingly, patients to have an endoscopic examination using the endoscope 2 according to the embodiment are less burdened and less painful.

Second Embodiment

Hereinafter, with reference to FIG. 8, a configuration of the insertion portion 6 according to the second embodiment of the present invention will be described.

Figure 8:
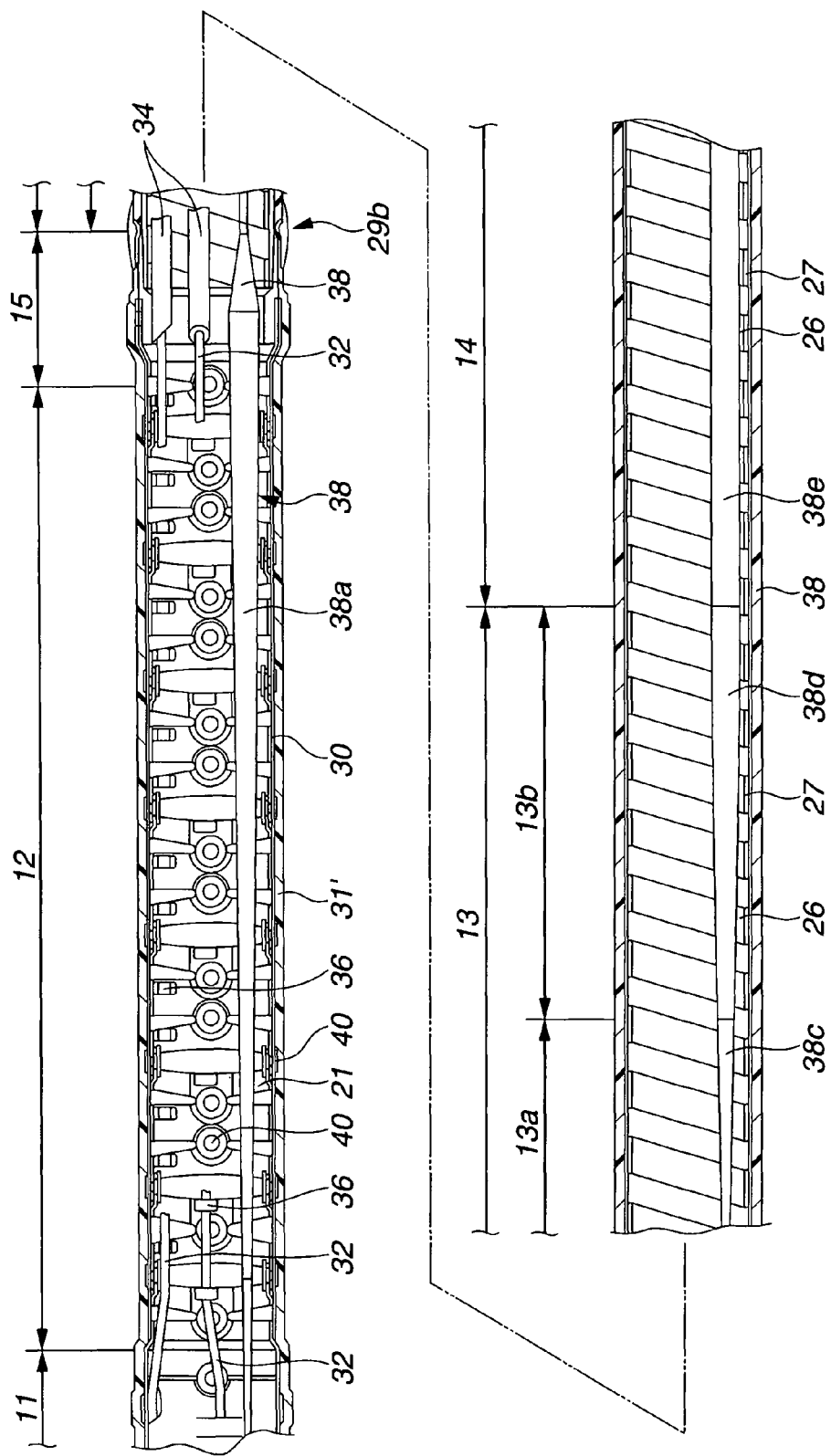
FIG. 8 is a cross sectional view of a distal end portion of an insertion portion cut along a longitudinal direction according to a second embodiment.

FIG. 8 is a cross sectional view of the distal end portion of the insertion portion cut along the longitudinal direction. In the descriptions of the present embodiment, with respect to similar configurations, operations, and advantages to those of the endoscope already described in the first embodiment, the same reference numerals are applied and their descriptions are omitted. Only different configurations, operations, and advantages will be mainly described.

As shown in FIG. 8, in the distal end configuration portion 11, the bending portion 12, the curvature transition portion 13, and the force quantity transmission portion 14 which constitute the insertion portion 6 of the endoscope 2 according to the present embodiment, a flexural rigidity adjustment rod 38 is inserted.

The flexural rigidity adjustment rod 38 includes, in order from the distal end, a bending portion adjustment portion 38a, a connection adjustment portion 38b, a first curvature transition portion adjustment portion 38c, a second curvature transition portion adjustment portion 38d, and a force quantity transmission portion adjustment portion 38e.

The bending portion adjustment portion 38a, and the first and second curvature transition portion adjustment portions 38c and 38d respectively have substantially cone shapes in which outer diameters of proximal end sides are constantly increased to outer diameters of distal end sides. The connection adjustment portion 38b has a substantially cone shape in which an outer diameter is constantly decreased from a distal end which has a substantially similar outer diameter of a most proximal end of the bending portion adjustment portion 38a toward a proximal end which has a substantially similar outer diameter of a most distal end of the first curvature transition portion adjustment portion 38c.

That is, the outer shape of the most distal end of the first curvature transition portion adjustment portion 38c is set to the diameter smaller than the outer diameter of the most proximal end of the bending portion adjustment portion 38a. The force quantity transmission portion adjustment portion 38e has a diameter similar to the outer diameter of the most proximal end of the second curvature transition portion adjustment portion 38d, and has a substantially cylindrical shape which has a fixed outer diameter from the distal end to the proximal end.

The outer cover 31 (see FIG. 3) which covers the bending portion 12 according to the first embodiment has the thickness which is gradually increased from the distal end side. An outer cover 31' which covers the bending portion 12 according to the present embodiment is formed to have a fixed thickness. Further, on the curvature transition portion 13 and the force quantity transmission portion 14 according to the present embodiment, instead of the respective outer covers 28a to 28c (see FIG. 3) of the first embodiment, a single outer cover 28 is covered over the whole portion.

The outer covers 31' and 28 have substantially similar flexibilities. Thus, the insertion portion 6 is set to have a fixed flexural rigidity by the respective flexural rigidities of the outer covers 31' and 28. That is, in the present embodiment, the variation of the flexural rigidity of the insertion portion 6 is set by the flexural rigidity adjustment rod 38.

Figure 9:
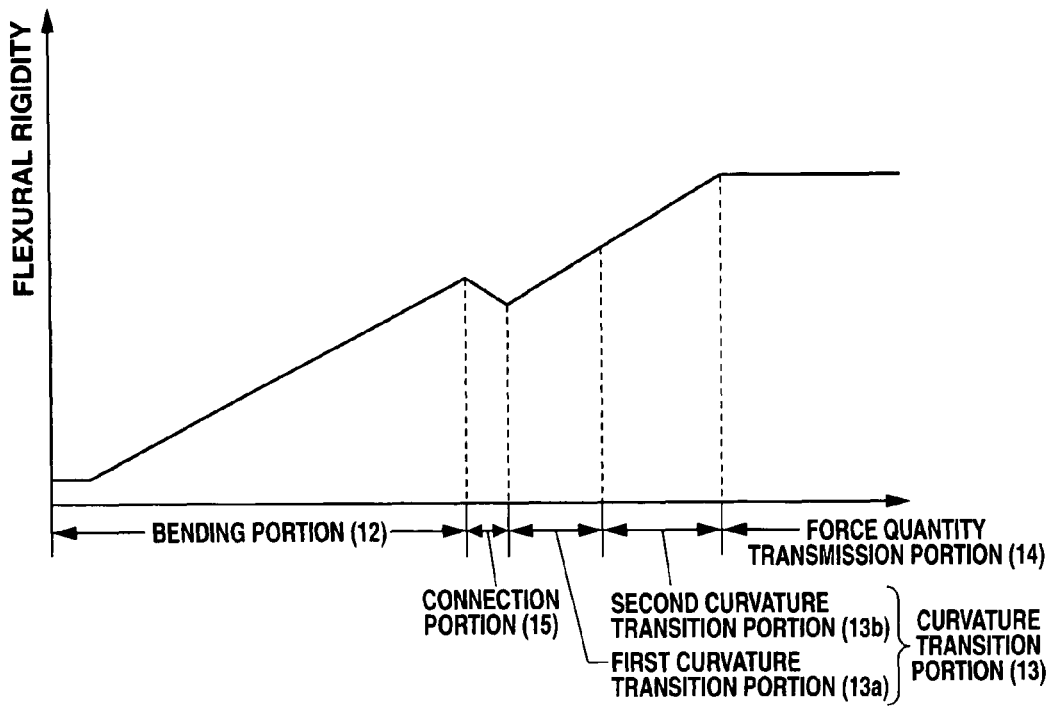
FIG. 9 is a graph illustrating variations of flexural rigidity of a bending portion, a curvature transition portion, and a flexible tube portion according to the second embodiment.

More particularly, as shown in the graph of FIG. 9, the flexural rigidity of the bending portion 12 is set such that corresponding to the flexural rigidity of the bending portion adjustment portion 38a of the flexural rigidity adjustment rod 38 which is inserted in the inside, from the distal end toward the proximal end to the connection portion 15, the flexural rigidity is continuously increased at a constant rate. Further, in the connection portion 15, the flexural rigidity is set such that corresponding to the flexural rigidity of the connection adjustment portion 38b of the inside, from a middle portion toward the proximal end to the distal end of the first curvature transition portion 13a, the flexural rigidity is continuously decreased at a constant rate.

The flexural rigidity from the distal end portion of the first curvature transition portion 13a to the proximal end of the second curvature transition portion is also set to be continuously increased at a constant rate, and the flexural rigidity at the most distal end of the first curvature transition portion 13a is set to be smaller than that of the most proximal end of the bending portion 12 by a predetermined value. The force quantity transmission portion 14 is configured to have a substantially similar flexural rigidity to the flexural rigidity of the curvature transition portion 13 of the most proximal end over the whole length.

Figure 10:
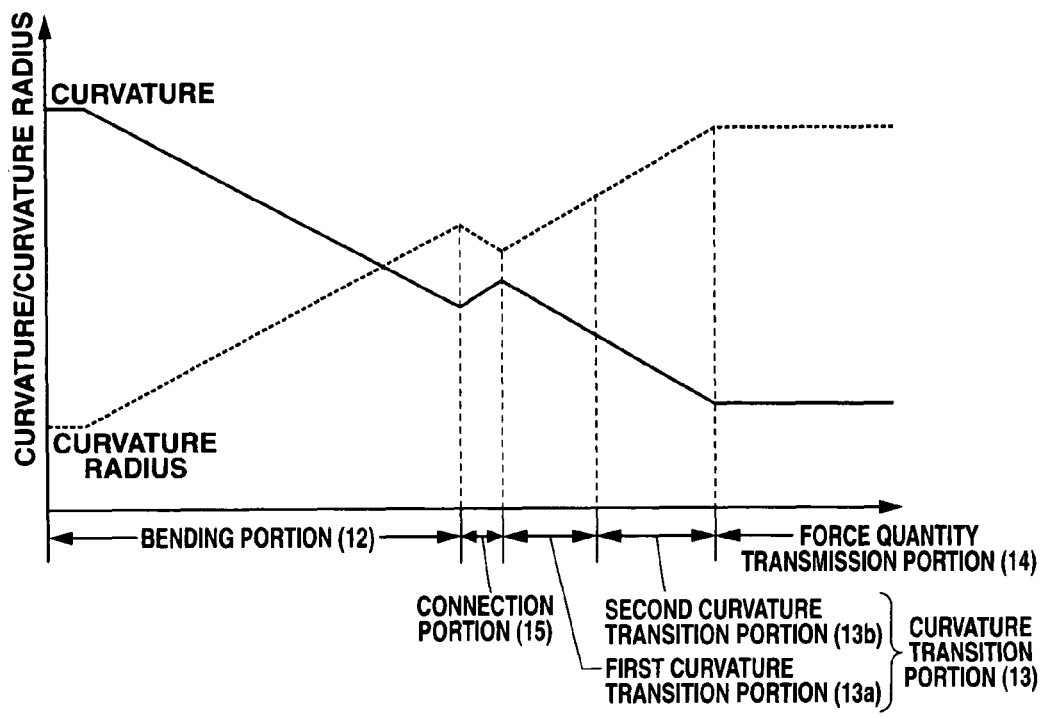
FIG. 10 is a graph illustrating variations of a curvature and a curvature radius at an insertion axis of a bending portion, a curvature transition portion, and a flexible tube portion according to the second embodiment.

That is, by a predetermined pressure force (for example, a force quantity of about 2 kg at a maximum), for example, in the bending portion 12 which is bent by a contact with a bending body cavity wall, as shown in the graph of FIG. 10, a curvature at the insertion axis of the most distal end is highest and a curvature at the insertion axis is continuously decreased at a predetermined rate to the connection portion 15.

In the similarly bent curvature transition portion 13, a curvature of the distal end portion of the first curvature transition portion 13a becomes higher by a predetermined value than that of the connection portion 15, then, at a constant rate, the curvature at the insertion axis is gradually decreased, and the curvature at the insertion axis at the most proximal end of the second curvature transition portion 13b becomes a smallest curvature.

In other words, in the insertion portion 6, the curvature radius at the insertion axis at the most distal end of the bending portion 12 which is bent by the contact with the body cavity wall which is bent by a predetermined pressure force (for example, a force quantity of about 2 kg at a maximum) becomes the smallest value. Then, in the insertion portion 6, the curvature radius at the insertion axis from the connection portion 15 to the distal end portion of the first curvature transition portion 13a becomes smaller than that of the most proximal end of the bending portion 12 by the predetermined value, and toward the proximal end, the curvature radius at the insertion axis is continuously increased at the constant rate.

Further, in the insertion portion 6, the curvature radius at the insertion axis at the most proximal end of the second curvature transition portion 13b of the curvature transition portion 13 becomes the largest value, and over the whole length of the force quantity transmission portion 14, the largest value of the curvature radius is constantly maintained.

Accordingly, since the distal end side of the first curvature transition portion 13a is set to be readily bent as compared with the bending state of the proximal end side of the bending portion 12, the curvature transition portion 13 is readily bent starting at the distal end side of the first curvature transition portion 13a.

As described above, into the inside of the insertion portion 6 of the endoscope 2 according to the present embodiment, the flexural rigidity adjustment rod 38 is inserted, and this enables to obtain similar advantages to those in the first embodiment.

Further, without providing the flexural rigidity adjustment rod 38 in the insertion portion 6, the forceps channel, the coil sheath, and the various endoscope conduits may be formed to have a similar outer diameter shape and thickness such that the flexural rigidity of the insertion portion 6 becomes the rate of change shown in FIG. 9.

Third Embodiment

Hereinafter, the third embodiment of the present invention will be described with reference to FIGS. 11 to 14.

Figure 11:
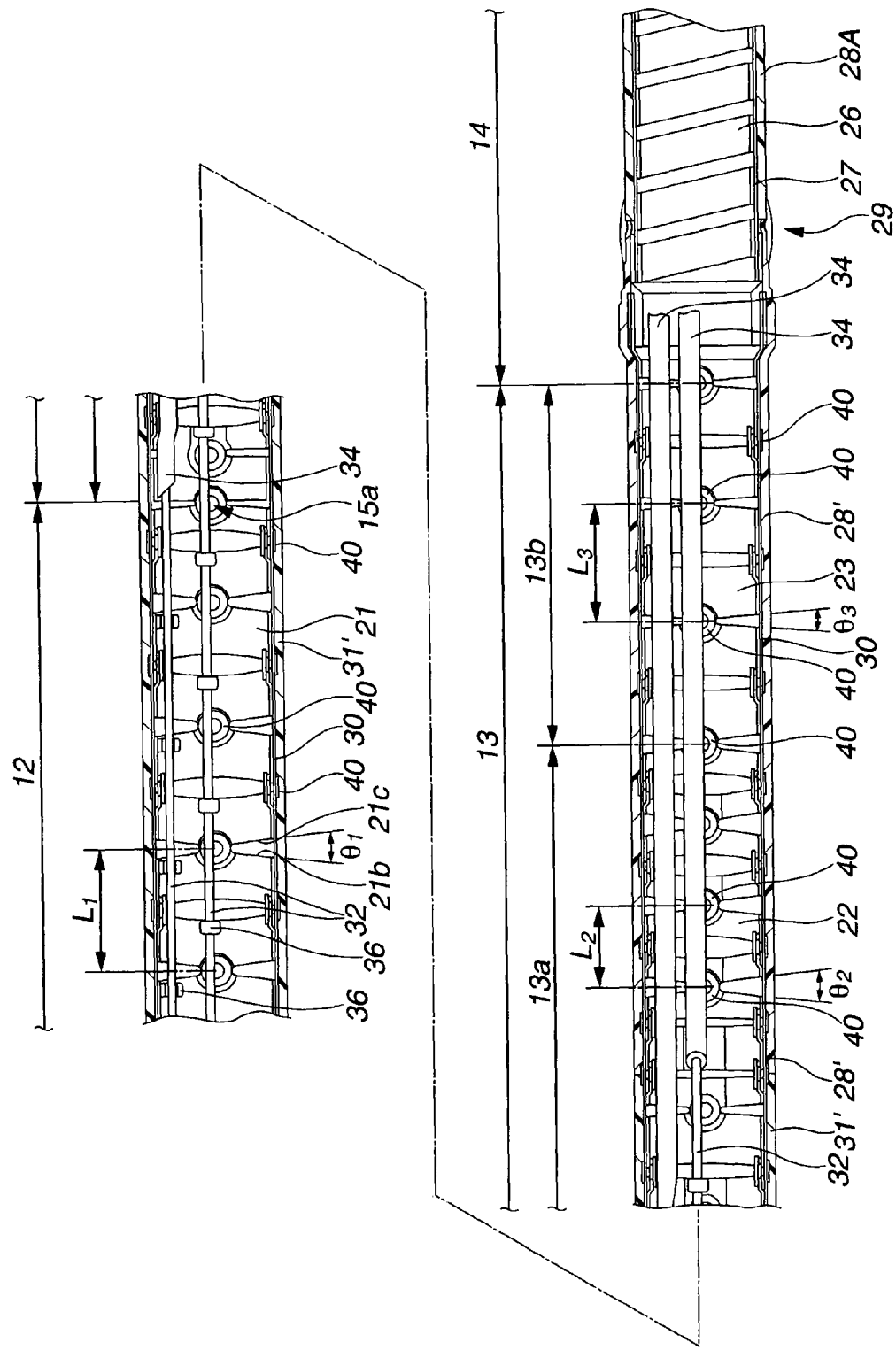
FIG. 11 is a cross sectional view of a distal end portion of an insertion portion cut along a longitudinal direction according to a third embodiment.
Figure 12:
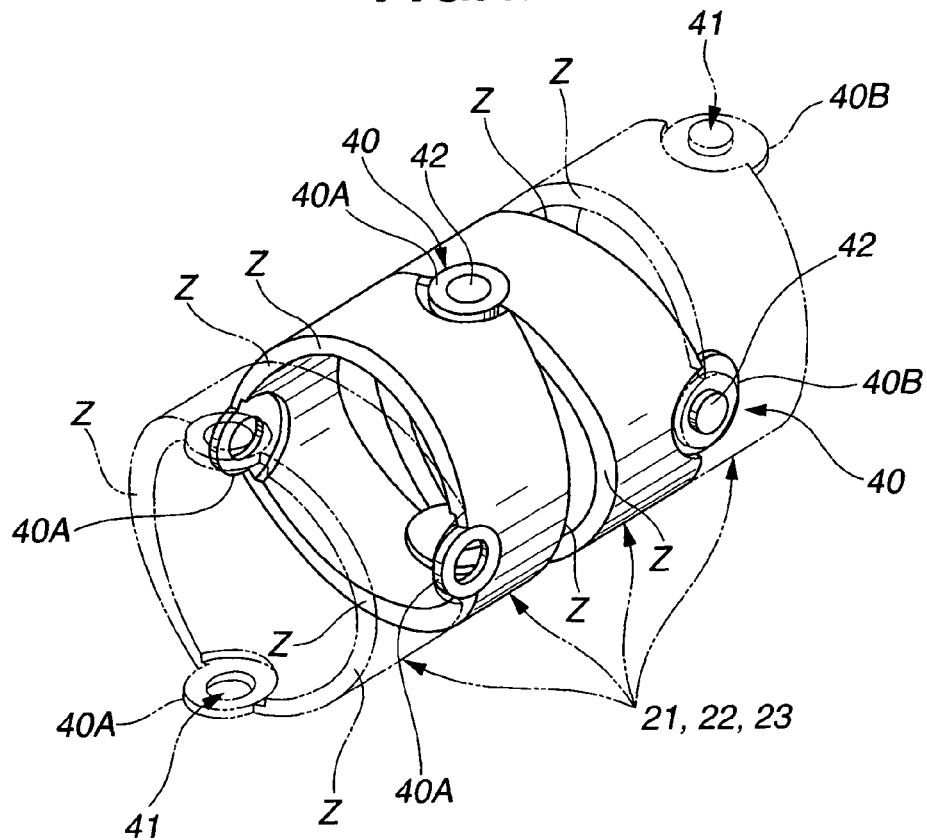
FIG. 12 is a perspective view for explaining respective pieces according to the third embodiment.
Figure 13:
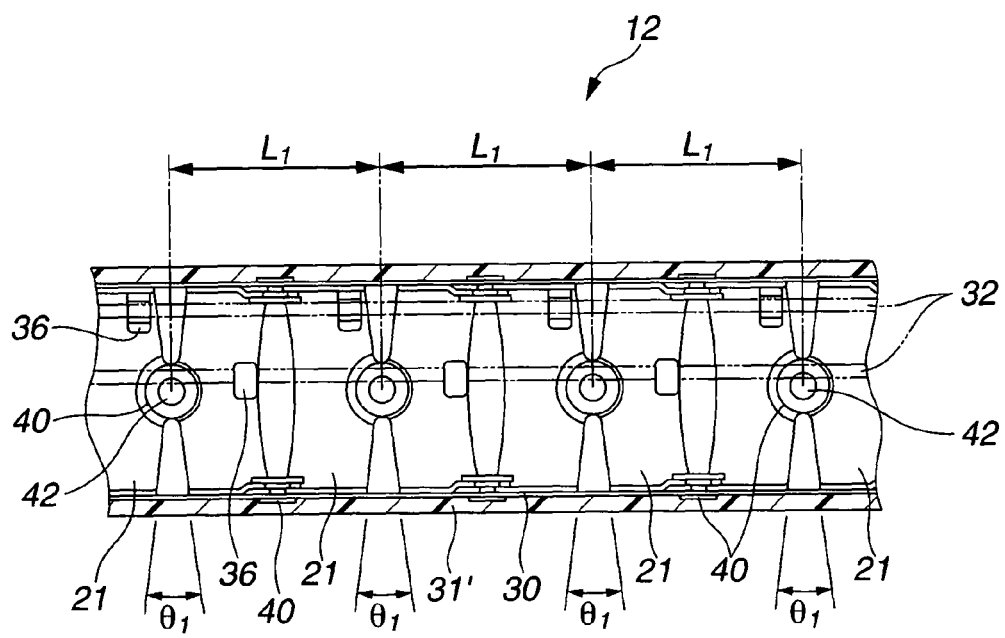
FIG. 13 is a cross sectional view of a bending portion in a state that an insertion axis is linear cut along a longitudinal direction according to the third embodiment.
Figure 14:
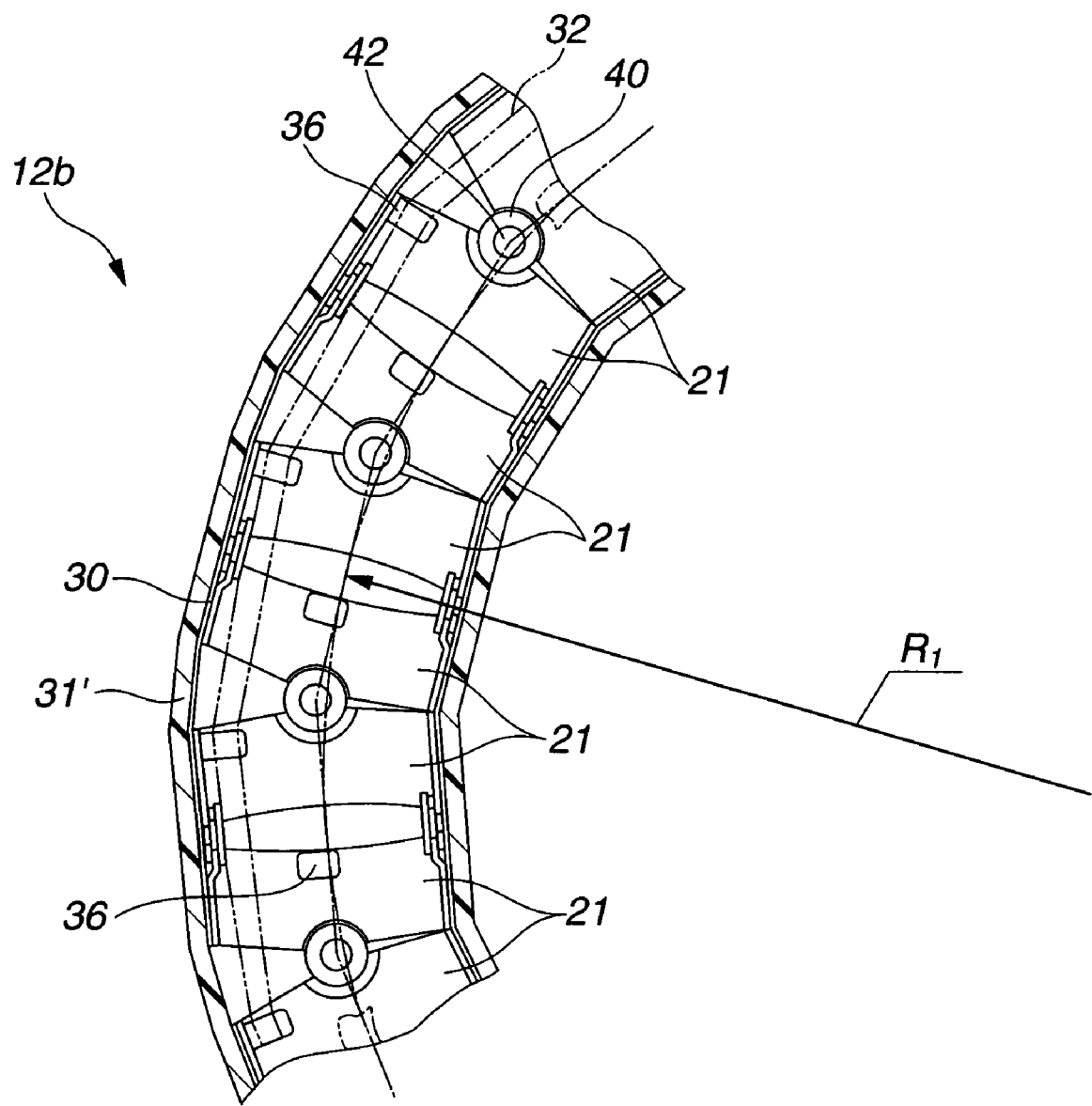
FIG. 14 is an enlarged view of the bending portion shown in FIG. 13 in a state that the bending portion is maximally bent in a downward direction according to the third embodiment.

FIG. 11 is a cross sectional view of the distal end portion of the insertion portion cut along the longitudinal direction, FIG. 12 is a perspective view for explaining respective pieces, FIG. 13 is a cross sectional view of the bending portion cut along the longitudinal direction in a state that the insertion axis is linear, FIG. 14 is an enlarged view of the bending portion shown in FIG. 13 in a state that the bending portion is bent to a maximum in the downward direction. In the descriptions of the present embodiment, with respect to similar configurations, operations, and advantages to those of the endoscope already described in the first and second embodiments, same reference numerals are applied and their descriptions are omitted. Only different configurations, operations, and advantages will be mainly described.

As shown in FIG. 11, the curvature transition portion 13 includes a plurality of first and second curvature regulation pieces 22 and 23 (also referred to as curvature regulation nodal rings) which will be described below. The plurality of the first and second curvature regulation pieces 22 and 23 are rotatably connected respectively by the joint portions 40 similarly to the bending pieces 21 of the bending portion 12.

In the present embodiment, the pieces which are provided with the above-described wire guides 36 are referred to as the bending pieces, and pieces which are not provided with the wire guides 36 are referred to as the curvature regulation pieces. That is, the plurality of bending pieces in the bending portion 12 have the wire guides 36 and the plurality of curvature regulation pieces in the curvature transition portion 13 do not have the wire guide 36.

With respect to a connection of the bending portion 12 and the curvature transition portion 13, in the inside of the respective border portions, the respective bending piece 21 and the curvature regulation piece 22 are rotatably connected such that rotation directions of the respective bending piece 21 and the curvature regulation piece 22 correspond to each other. More specifically, between the bending portion 12 and the curvature transition portion 13 in the insertion portion 6 of the endoscope 2 according to the present embodiment, a portion where the bending piece 21 and the curvature regulation piece 22 which rotate for a bending in the vertical direction are connected shown in FIG. 11 is referred to as a connection portion 15*a*.

In the endoscope 2 according to the present embodiment, since the bending portion 12 is bendable in the four directions of vertical and horizontal directions, a portion where respective bending piece 21 and the curvature regulation piece 22 which rotate for a bending in the horizontal direction substantially orthogonal to the vertical direction is also to be the connection portion. That is, the endoscope 2 according to the present embodiment includes two connection portions (15*a*) where the respective bending pieces and the respective curvature regulation pieces are connected one another.

In the present embodiment, the respective bending pieces 21 and the respective curvature regulation pieces 22 which are disposed at the border of the bending portion 12 and the curvature transition portion 13 may be connected not in the rotatable state but in a fixed state.

The curvature transition portion 13 is formed such that on the plurality of the curvature regulation pieces 22 and 23, the bending braid 30 from the bending portion 12 described in the first embodiment is covered, and on the bending braid 30, the outer cover 28' is covered to maintain water tightness. The outer cover 28' has a similar flexibility to that of the outer cover 31' described in the second embodiment. Accordingly, the bending portion 12 and the curvature transition portion 13 have a predetermined flexural rigidity such that the respective flexural rigidities become equal to each other by the respective outer covers 31' and 28'.

The outer cover 31' of the bending portion 12 covers, in the present embodiment, to the border portion between the bending portion 12 and the first curvature transition portion 13*a*. The outer cover 31' may integrally cover the whole length of the bending portion 12 and the curvature transition portion 13.

As shown in FIG. 12, the respective bending pieces 21 and the respective curvature regulation pieces 22 and 23 are formed by substantially cylindrical short tubes respectively. At respective one ends of the respective bending pieces 21 and the respective curvature regulation pieces 22 and 23, here, at distal end sides, pairs of pivotally supporting portions 40A for rotatably connecting with respect to adjacent pieces are provided. The pairs of pivotally supporting portions 40A are provided at positions dividing circumferences of the respective bending pieces 21 and the respective curvature regulation pieces 22 and 23 in half, that is, positions shifted by 180 degrees in a circumferential direction around the insertion axis each other.

At respective other ends of the respective bending pieces 21 and the respective curvature regulation pieces 22 and 23, here, at proximal end sides, similarly to the one end sides, pairs of pivotally supporting portions 40B are provided being shifted to the inner circumferential sides by thickness of the plates. That is, in the respective bending pieces 21 and the respective curvature regulation pieces 22 and 23, the respective pivotally supporting portions 40A and 40B of the one end sides and the other end sides are overlapped with each other. Into hole portions 41 formed on the pivotally supporting portions 40A and 40B, pivot members 42 such as rivets are inserted to pivotally support the respective bending pieces 21 and the respective curvature regulation pieces 22 and 23.

In the respective one bending pieces 21 and the curvature regulation pieces 22 and 23, the pair of pivotally supporting portions 40A of the one end side is provided at a position shifted by 90 degrees in the circumferential direction around the insertion axis each other with respect to the pair of the pivotally supporting portions 40B of the other side. That is, in the respective single bending pieces 21 and the curvature regulation pieces 22 and 23, the pair of pivotally supporting portions 40A of the one end side is provided at the position in a direction orthogonal to a line connecting pivots of the respective pivot members 42, a line connecting the pair of the pivotally supporting portions 40B of the other end side, and the insertion axis.

Accordingly, the connected respective bending pieces 21 and curvature regulation pieces 22 and 23 are connected such that the respective bending pieces 21 and curvature regulation pieces 22 and 23 can rotate, at the one end side, in the two circumferential directions around the axis of the respective pivot members 42 of the pivotally supporting portions 40A and at the other end side, in the two circumferential directions around the axis of the pivot members 42 of the pivotally supporting portions 40B orthogonal to the above two directions and the insertion axis. In the description of the present embodiment, the pivotally supporting portions 40A and 40B, and the pivot member 42 constitute the joint portions 40.

The respective bending pieces 21 and the respective curvature regulation pieces 22 and 23 are annular members being connected with adjacent pieces through the joint portions 40. The respective bending pieces 21 and the respective curvature regulation pieces 22 and 23 are annular members which have, as described above, the pivotally supporting portions 40A and 40B which are so-called auricular portions protruded from the respective both end surfaces to have surfaces to oppose to each other, and formed in a mountain-shaped cut with an apex of the pivotally supporting portions 40A and 40B to have shorter length in the axis direction.

Further, the respective bending pieces 21 and the respective curvature regulation pieces 22 and 23 are connected one another such that when the respective end surface of the one end side or the other end side is rotated by the pivotally supporting portions 40A and 40B, some parts of the respective end surfaces (for example, a end surface 21b of the bending piece 21 shown in FIG. 11) comes in contact with some parts of the respective opposed surface (for example, a end surface 21c of the bending piece 21 shown in FIG. 11) of adjacent pieces.

In descriptions below, the portions where the respective end surfaces come in contact with the respective opposed surfaces of the adjacent pieces in response to the rotation of the respective pieces 21, 22, and 23 are referred to as contact portions Z (see FIG. 12). The contact portions Z exist on the both end surfaces of the respective pieces 21, 22, and 23 shifted by about 90 degrees in the circumferential direction around the insertion axis each other with respect to the two joints 40 of the respective connected pieces 21, 22, and 23. The both end surfaces of the respective pieces 21, 22, and 23 are formed in the mountain-shaped cut toward central portion sides of the outer shapes such that the respective contact portions Z and the respective contact portions Z of the adjacent pieces are spaced apart by predetermined distances.

That is, the respective bending pieces 21 and the respective curvature regulation pieces 22 and 23 in which the bending portion 12 and the curvature transition portion 13 are substantially linear state are respectively connected to have the predetermined spaces between the contact portions Z which correspond and come in contact with each other as described above. In the respective bending pieces 21 and the respective curvature regulation pieces 22 and 23 according to the present embodiment, the both end surfaces are not limited to be formed in the mountain-shaped cut toward the central portion sides of the outer shapes but may be formed in any shape if the predetermined spaces can be provided between the respective contact portions Z in the state that the pieces are connected with each other.

Now, the connection state of the respective bending pieces 21 and the respective curvature regulation pieces 22 and 23 will be described.

First, in the state that the insertion axis of the bending portion 12 is linear, with an apex of a rotation axis center common between the rotating and contacting two bending pieces, a contained angle of the lines connecting the respective contact portions Z (see FIG. 12) to the apex is set to a predetermined angle θ1. In the bending portion 12, the pair of joints 40 which have the parallel pivot member 42 in the axis direction is configured such that with respect to the longitudinal direction of the bending portion 12, a space between the axes of the pivot members 42 is spaced apart by a predetermined distance L1.

Further, in the state that the insertion axis of the first curvature transition portion 13a is linear, with an apex of a rotation axis center common between the rotating and contacting two first curvature regulation pieces, a contained angle of the lines connecting the respective contact portions Z (see FIG. 12) to the apex is set to a predetermined angle θ2. In the first curvature transition portion 13a, the pair of joints 40 which have the parallel pivot member 42 in the axis direction is configured such that with respect to the longitudinal direction of the first curvature transition portion 13a, a space between the axes of the pivot members 42 is spaced apart by a predetermined distance L2.

Further, in the state that the insertion axis of the second curvature transition portion 13b is linear, with an apex of a rotation axis center common between the rotating and contacting two second curvature regulation pieces 23, a contained angle of the lines connecting the respective contact portions Z (see FIG. 12) to the apex is set to a predetermined angle θ3. In the second curvature transition portion 13b, the pair of joints 40 which have the parallel pivot in the axis direction is configured such that with respect to the longitudinal direction of the second curvature transition portion 13b, a space between the axes of the pivot members 42 is spaced apart by a predetermined distance L3.

The connection portion of the first curvature transition portion 13a and the second curvature transition portion 13b is rotatably connected by the pair of joint portions 40 of the first curvature regulation piece 22 of the most proximal end and the pair of joint portions 40 of the second curvature regulation piece 23 of the most distal end.

Further, the bending piece 21 of the most proximal end and the first curvature regulation piece 22 of the most distal end are rotatably connected at the border portion between the bending portion 12 and the first curvature transition portion 13a by the pair of joint portions 40 of the bending piece 21 of the most proximal end and the pair of joint portions 40 of the first curvature regulation piece 22 of the most distal end.

In the force quantity transmission portion 14, similarly to the first embodiment, the flex tube 26 which is the spiral tube is inserted. On the outer circumference of the flex tube 26, similarly to the bending portion 12 and the curvature transition portion 13, the braid 27 is covered. Further, on the outer circumference of the braid 27, an outer cover 28A which has a lower flexibility than that of the outer cover 31', that is, which has a high flexural rigidity, and which is to be the second exterior tube body is covered.

Accordingly, the force quantity transmission portion 14, in order to adequately transmit a pressure force quantity at the proximal end side to the distal end of the insertion portion 6, has a lower flexibility as compared to the bending portion 12 and the curvature transition portion 13. That is, the force quantity transmission portion 14 is set to have a higher flexural rigidity than those of the bending portion 12 and the curvature transition portion 13. Between the curvature transition portion 13 and the force quantity transmission portion 14, a spool-adhesion portion 29 which adherers the outer cover 28' and the outer cover 28A by a spool is provided.

Now, descriptions will be made with respect to respective curvatures and respective curvature radius in a state that the bending portion 12 and the curvature transition portion 13 are maximally bent with reference to FIGS. 13 and 14. In the description about the respective curvatures and the respective curvature radius, the cross sectional view of the bending portion 12 cut along the longitudinal direction is used.

As described above, in the sate that the insertion axis of the bending portion 12 is linear, with the apex of the rotation axis center common between the rotating and contacting two bending pieces 21, the contained angle of the lines connecting the respective contact portions Z (see FIG. 12) to the apex is set to the predetermined angle θ1. Further, in the bending portion 12, the pair of joints 40 which have the parallel pivot member 42 in the axis direction is configured such that with respect to the longitudinal direction of the bending portion 12, the space between the axis of the pivot member 42 is spaced apart by the predetermined distance L1.

As shown in FIG. 14, the bending portion 12 becomes the maximally bending state in a state that the peripheral end portions (contact portions Z) of a side where the adjacent respective bending pieces 21 are bending come in contact with each other. More specifically, the respective bending pieces 21 are moved such that, with respect to the bending direction, in the circumferential direction around the axis of the pivot member 42 of the joint 40 which is to be a rotation axis, the peripheral end portions (contact portions Z) of the inside than the insertion axis which draws an arc by the bending of the bending portion 12 come closer respectively. Then, in the respective bending pieces 21, the peripheral end portions (contact portions Z) of the inside than the insertion axis which draws an arc come in contact with each other, and the rotation in the circumferential direction around the axis of the joint 40 is inhibited.

Accordingly, the bending portion 12 functions as a stopper when the respective peripheral end portions (contact portions Z) of the bending pieces 21 come in contact with each other. Then, the state that the rotation in the circumferential direction around the axis of the joint 40 is inhibited becomes the maximum bending state of the bending portion 12.

A curvature radius R1 at the insertion axis of the maximally bent bending portion 12 is set, in the state that the insertion axis of the bending portion 12 is linear, according to a relationship between the predetermined angle θ1 which is formed by the opposed surfaces of the two adjacent bending pieces 21 and the distance L1 between the respective axes in which the axes directions of the pivot members 42 are parallel. That is, a curvature C1 which is an inverse number of the curvature radius R1 at the insertion axis of the maximally bent bending portion 12 is also set, in the state that the insertion axis of the bending portion 12 is linear, with the apex of the rotation axis center common between the adjacent two bending pieces 21, according to the relationship between the contained angle of the lines connecting the respective contact portions Z (see FIG. 12) to the apex, that is, the predetermined angle θ1, and the distance L1 between the axes of the pivot members 42 in the parallel axis direction with respect to the longitudinal direction of the bending portion 12.

The curvature C1 and the curvature radius R1 at the insertion axis at the maximally bending state of the bending portion 12 can be calculated by the following equation (1).

$$C1=1/R1\approx(2 \tan \theta 1/2)/L1 \qquad (1)$$

The first curvature transition portion 13a becomes a maximum bending state in a state that the peripheral end portions (contact portions Z) of the bending side of the adjacent respective first curvature regulation pieces 22 come in contact with each other. More particularly, the respective first curvature regulation pieces 22 are moved such that, with respect to the bending direction, in the circumferential direction around the axis of the pivot member 42 of the joint 40 which is to be the rotation axis, the peripheral end portions (contact portions Z) of the inside than the insertion axis which draws an arc by the bending of the curvature transition portion 13a come closer respectively. Then, in the respective first curvature regulation pieces 22, the peripheral end portions (contact portions Z) of the inside than the insertion axis which draws the arc come in contact with each other, and the rotation in the circumferential direction around the axis of the joint 40 is inhibited.

Accordingly, the first curvature transition portion 13a functions as a stopper when the respective peripheral end portions (contact portions Z) of the first curvature regulation pieces 22 come in contact with each other. Then, the state that the rotation in the circumferential direction around the axis of the joint 40 is inhibited becomes the maximum bending state of the first curvature transition portion 13a.

A curvature C2 and a curvature radius R2 at the insertion axis at the maximally bent state of the first curvature transition portion 13a are set, in the state that the insertion axis of the first curvature transition portion 13a is linear, with an apex of the rotation axis center common between the adjacent two first curvature regulation pieces 22, according to a relationship between a predetermined angle θ2 which is a contained angle of the lines connecting the respective contact portions Z (see FIG. 12) with the apex, and the distance L2 between the axes of the pivot members 42 which is in the axis direction parallel to the longitudinal direction of the first curvature transition portion 13a.

The curvature C2 and the curvature radius R2 at the insertion axis at the maximally bending state of the first curvature transition portion 13a can be calculated by the following equation (2).

$$C2=1/R2\approx(2 \tan \theta 2/2)/L2 \qquad (2)$$

The second curvature transition portion 13b becomes a maximum bending state in a state that the peripheral end portions (contact portions Z) of the bending side of the adjacent respective second curvature regulation pieces 23 come in contact with each other. More particularly, the respective second curvature regulation pieces 23 are moved such that, with respect to the bending direction, in the circumferential direction around the axis of the pivot member 42 of the joint 40 which is to be the rotation axis, the peripheral end portions (contact portions Z) of the inside than the insertion axis which draws an arc by the bending of the curvature transition portion 13b come closer respectively. Then, in the respective second curvature regulation pieces 23, the peripheral end portions (contact portions Z) of the inside than the insertion axis which draws the arc come in contact with each other, and the rotation in the circumferential direction around the axis of the joint 40 is inhibited.

Accordingly, the second curvature transition portion 13b functions as a stopper when the respective peripheral end portions (contact portions Z) of the second curvature regulation pieces 23 come in contact with each other. Then, the state that the rotation in the circumferential direction around the axis of the joint 40 is inhibited becomes the maximum bending state of the second curvature transition portion 13b.

A curvature C3 and a curvature radius R3 at the insertion axis at the maximally bending state of the second curvature transition portion 13b are set, in the state that the insertion axis of the second curvature transition portion 13b is linear, with an apex of the rotation axis center common between the adjacent two second curvature regulation pieces 23, according to a relationship between a predetermined angle θ3 which is a contained angle of the lines connecting the respective contact portions Z (see FIG. 12) with the apex, and the distance L3 between the axes of the pivot members 42 which is in the axis direction parallel to the longitudinal direction of the second curvature transition portion 13b.

The curvature C3 and the curvature radius R3 at the insertion axis at the maximally bending state of the second curvature transition portion 13b can be calculated by the following equation (3).

$$C3 = 1/R3 \approx (2 \tan \theta 3/2)/L3 \qquad (3)$$

As described above, in the bending portion 12, the first curvature transition portion 13a, and the second curvature transition portion 13b according to the present invention, the respective angles θ1 to θ3, and the respective distances L1 to L3 are set such that the relationship of the respective curvatures at the respective insertion axes at the maximally bending state is to be C3<C1<C2.

In other words, in the bending portion 12, the first curvature transition portion 13a, and the second curvature transition portion 13b, the respective angles θ1 to θ3, and the respective distances L1 to L3 are set such that the relationship of the respective curvature radiuses at the respective insertion axes at the maximally bending state is to be R2<R1<R3.

Accordingly, the insertion portion 6 of the endoscope 2, in the bending portion 12 to the second curvature transition portion 13b, the curvatures of the respective portions at the maximally bending state are set such that the curvature of the first curvature transition portion 13a is set to be larger than that of the bending portion 12, and the curvature of the second curvature transition portion 13b is set to be smaller than that of the first curvature transition portion. Further, the curvature of the second curvature transition portion 13b is set to be smaller than that of the bending portion 12.

In other words, when the bending portion 12, the first curvature transition portion 13a, and the second curvature transition portion 13b are maximally bent respectively, the first curvature transition portion 13a is bent at a smaller curvature radius than that of the bending portion 12. Then, the curvature radius of the second curvature transition portion 13b is set to vary to a larger radius than that of the bending portion 12, and the second curvature transition portion 13b is bent.

Further, in the present embodiment, the three steps of the curvature radiuses at the maximally bending state of the bending portion 12, the first curvature transition portion 13a, and the second curvature transition portion 13b are set. However, variations of the radiuses may be set to be closer, for example, four steps or six steps such that the curvature radiuses from the bending portion 12 to the second curvature transition portion 13b are smoothly varied.

Further, from the bending portion 12 to the second curvature transition portion 13b, with the apex of the rotation axis center common among the adjacent respective pieces, the predetermined angles θ2 to θ3 which are the contained angles of the lines connecting the respective contact portions Z (see FIG. 12) to the apex, and the lengths of the respective distances L2 to L3 between the pivot members 42 may be set to be finer values to vary the sizes with respect to each piece in order to vary the curvature radiuses at substantially no step from the bending portion 12 to the second curvature transition portion 13b at the maximally bending state.

Further, as described above, the force quantity transmission portion 14 of the insertion portion 6 has the higher flexural rigidity than those of the bending portion 12 and the curvature transition portion 13. That is, the force quantity transmission portion 14 of the insertion portion 6 has the lower flexibility than those of the bending portion 12 and the curvature transition portion 13.

As a result, also in the insertion portion 6 according to the present embodiment, the distal end side of the first curvature transition portion 13a is set to readily bend than the bending state of the bending portion 12. Accordingly, starting at the first curvature transition portion 13a, the curvature transition portion 13 is readily bent. Thus, the endoscope 2 according to the present embodiment can obtain similar advantages to those of the first and second embodiments.

In the above-described respective embodiments, the insertion portion 6 may be configured without the force quantity transmission portion 14 to have only the distal end configuration portion 11, the bending portion 12, and the curvature transition portion 13.

Although the present invention has been described with reference to the above-described embodiments, it is noted that various modifications may be employed without departing from the scope of the invention.

The invention claimed is:

1. An endoscope having an insertion portion to be inserted into a body cavity, the endoscope comprising:
   a bending portion provided at a distal end side of the insertion portion and configured to be actively bendable in accordance with a bending operation of an operator, the bending portion including inside thereof a plurality of annular bending pieces rotatably connected to each other by a first set of pivots, the bending portion including a first region in which opposed peripheral portions of adjacent bending pieces are in contact with each other at a first curvature radius at which the bending portion is maximally bent;
   a first flexible tube portion connected to a proximal end side of the bending portion, and configured not to be actively bendable in accordance with the bending operation of the operator, but to be passively bent by a provided predetermined force quantity, the first flexible tube portion including inside thereof a plurality of annular curvature regulation pieces rotatably connected to each other by a second set of pivots, the first flexible tube portion including a second region which is regulated with opposed peripheral portions of adjacent curvature regulation pieces being into contact with each other, is disposed at a distal end side, and is maximally bent at a second curvature radius smaller than the first curvature radius, and a third region which is connected at a more proximal end side than the second region and is maximally bent at a third curvature radius larger than the second curvature radius; and
   a second flexible tube portion composed of a spiral tube connected to a proximal end side of the first flexible tube portion,
   a braid covering an outer circumference of the first flexible tube portion and the second flexible tube, and
   an outer cover resin coveting the braid, the outer cover resin having a first outer cover resin portion coveting the second region and having a first flexibility and a second cover resin portion covering the third region and having a second flexibility that is different from the first flexibility,
   wherein the first outer cover resin and the second outer cover resin are configured to increase a flexural rigidity of the first flexible tube portion from the distal end side to the proximal end side.

2. The endoscope according to claim 1, wherein
   a flexural rigidity of an outer cover resin which covers an outer circumference of the region that is maximally bent at the second curvature radius and an outer circumference of the region that is maximally bent at the third curvature radius in the first flexible tube portion are similar to or less than a flexural rigidity of an outer cover resin which covers an outer circumference of the bending portion, and
   a flexural rigidity of an outer cover resin which covers the second flexible tube portion is larger than the flexural rigidity of the outer cover resin which covers the outer circumference of the bending portion.

* * * * *